United States Patent [19]

Vertesy et al.

[11] Patent Number: 5,763,397
[45] Date of Patent: Jun. 9, 1998

[54] GLYCOPEPTIDES, A PROCESS FOR THEIR PREPARATION AND THEIR USE

[75] Inventors: László Vertesy, Eppstein/Taunus; Joachim Betz, Frankfurt am Main; Hans-Wolfram Fehlhaber, Idstein; Michael Limbert, Hofheim am Taunus, all of Germany

[73] Assignee: Hoechst Aktiengesellschaft, Frankfurt am Main, Germany

[21] Appl. No.: 907,747

[22] Filed: Jun. 29, 1992

[30] Foreign Application Priority Data

Jun. 29, 1991 [DE] Germany ............ 41 21 662.8
Oct. 19, 1991 [DE] Germany ............ 41 34 611.4

[51] Int. Cl.⁶ .............. A61K 38/12; A61K 38/14; C12P 19/60; C12N 1/22
[52] U.S. Cl. .............. 514/9; 514/8; 530/317; 530/322; 530/323; 435/75; 435/252.1; 435/822
[58] Field of Search .............. 514/8, 9; 530/317, 530/322, 323; 435/75, 252.1, 822

[56] References Cited

U.S. PATENT DOCUMENTS 4,584,300  4/1986  Iwao et al.
4,908,364  3/1990  Thorwart et al.
4,929,643  5/1990  Lang et al.
5,591,714  1/1997  Nararajan et al. .......... 514/9

FOREIGN PATENT DOCUMENTS 0 187 772 A2  7/1986  European Pat. Off.
0 468 504 A1  1/1992  European Pat. Off.

OTHER PUBLICATIONS

Ramakrishnan Nagarajan, "Antibacterial Activities and Modes of Vancomycin and Related Glycopeptides," Apr. 1991, pp. 605–609, Antimicrobial Agents an Chemotherapy. STN ACS Chem Abs 116(1):6973(e) Nagarajan et al Jul. 3, 1991 (Priority US89–449171 Dec. 13, 1989).

Primary Examiner—Herbert J. Lilling
Attorney, Agent, or Firm—Finnegan, Henderson, Farabow, Garrett & Dunner, L.L.P.

[57] ABSTRACT

Desmethylbalhimycin, a compound of the formula $C_{65}H_{71}Cl_2N_9O_{24}$, desmethylleucylbalhimycin, a compound of the formula $C_{59}H_{60}Cl_2N_8O_{23}$, desglucobalhimycin, a compound of the formula $C_{60}H_{63}Cl_2N_9O_{19}$, ureidobalhimycin, a compound of the formula $C_{67}H_{74}Cl_2N_{10}O_{25}$, desmethyl-desglucobalhimycin, a compound of the formula $C_{59}H_{61}Cl_2N_9O_{19}$ and balhimycin V, a compound of the formula $C_{73}H_{84}Cl_2N_{10}I_{26}$, methylbalhimycin, a compound of the formula $C_{67}H_{75}Cl_2N_9O_{24}$ and balhimycin R, a compound of the formula $C_{72}H_{83}Cl_2N_9O_{28}$, have an antibiotic action.

12 Claims, No Drawings

GLYCOPEPTIDES, A PROCESS FOR THEIR PREPARATION AND THEIR USE

The present invention relates to novel glycopeptides, a process for their preparation and their use.

A large number of glycopeptide antibiotics have already been described. However, many of these antibiotics are more weakly active than the original type of glycopeptides and commercial product vancomycin and are inferior to this, in particular also in vivo (cf. R. Nagarajan Antimicrobial Agents and Chemotherapy, April 1991, pages 605–609).

Vancomycin may indeed be employed in infectious diseases which are caused by gram-positive pathogens, but a number of severe side effects, such as, for example, the so-called "red man syndrome", sphacelation and others greatly restrict the applicability. Another very active glycopeptide antibiotic is balhimycin (cf. EP 0 468 504, to which reference is expressly made at this position).

It has now surprisingly been found that strongly active antibiotic substances can be made available with the compounds related to balhimycin, the side effects known from vancomycin not occurring or occurring in diminished form.

The invention accordingly relates to desmethylbalhimycin, a compound of the formula I,

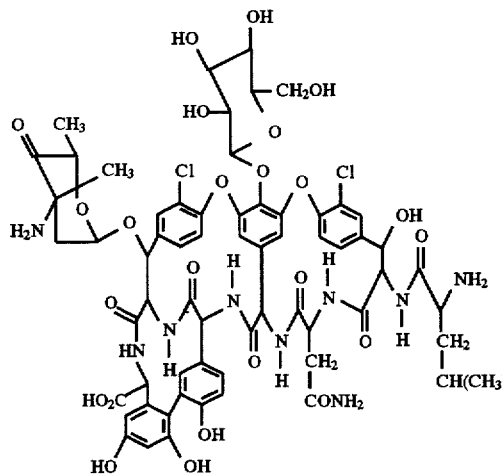

desmethylleucylbalhimycin, a compound of the formula II.

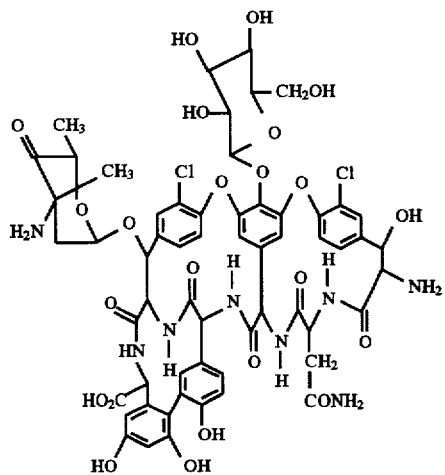

desglucobalhimycin, a compound of the formula III,

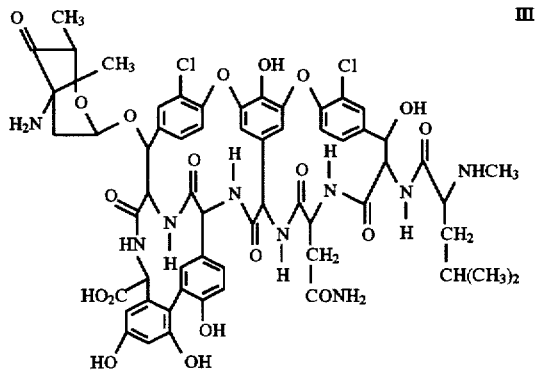

ureidobalhimycin, a compound of the formula IV,

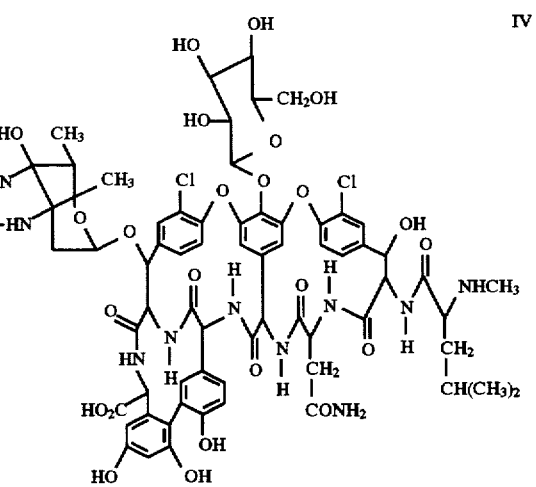

desmethyl-desglucobalhimycin, a compound of the formula V,

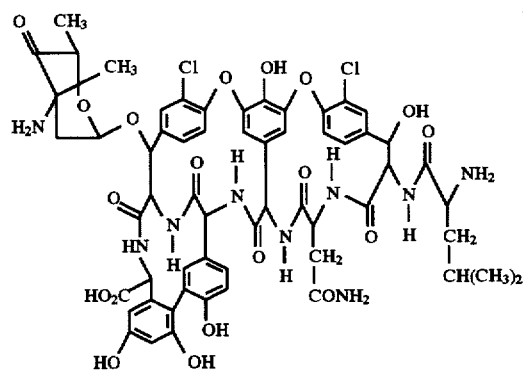

methylbalhimycin, a compound of the formula $C_{67}H_{75}Cl_2N_9O_{24}$, balhimycin R, a compound of the formula $C_{72}H_{83}Cl_2N_9O_{28}$ and balhimycin V, a compound of the formula $C_{73}H_{84}Cl_2N_{10}O_{26}$ and their hydrates and physiologically tolerable salts.

The hydrates of the compounds mentioned are formed by addition of water, such as shown below by the example of desmethylbalhimycin.

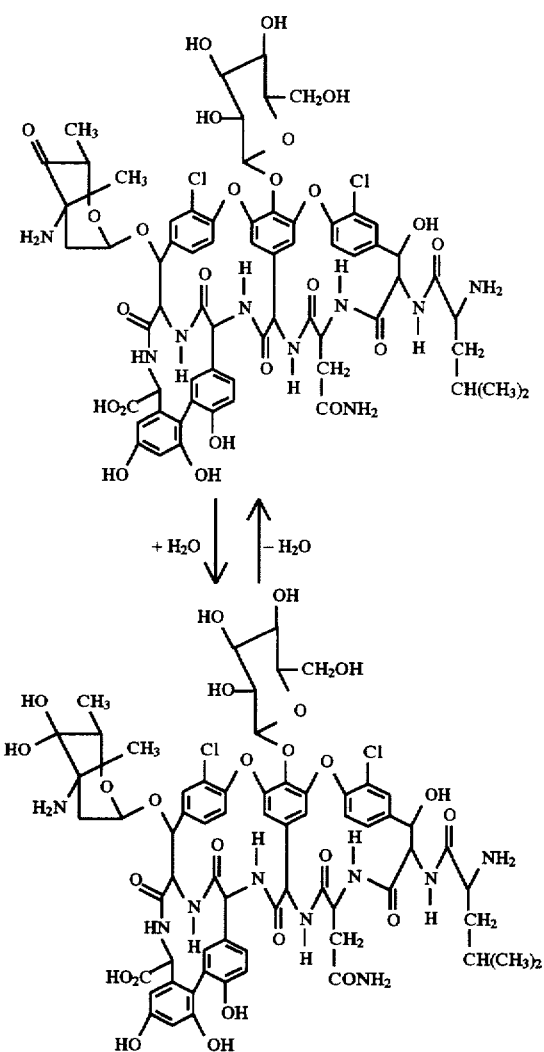

Physiologically tolerable salts of the compounds mentioned are, for example, the acetates, hydrochlorides, phosphates, sulfates, etc., which can be obtained in a generally known manner.

The present invention furthermore includes the process for the preparation of the compounds mentioned. A process for the preparation of the compounds mentioned is characterized in that the microorganism Actinomyces species Y-86, 21022 (DSM 5908) is cultured in an aqueous nutrient medium and the target compounds are then isolated and purified. The microorganism mentioned has been deposited on Apr. 6, 1990 under the conditions of the Budapest Convention.

The microorganism mentioned is cultured as described in the abovementioned EP in an aqueous nutrient medium containing carbon sources, nitrogen sources and mineral salts. Preferred culturing conditions are described in the abovementioned EP; further preferred conditions are mentioned in the example below.

During culturing of the microorganism mentioned, balhimycin and, in only small amounts, the abovementioned compounds are mainly formed. By variation of the nutrient base composition, in particular with respect to the nitrogen source, the formation of distinctly larger amounts of the compounds according to the invention can be achieved. Thus, it has surprisingly been found that the addition of millimolar concentrations of methionine, serine and pyruvate suppresses the formation of balhimycin. If methionine antagonists, such as, for example, 1 mM α-methylmethionine, are employed, a distinct increase in the yields takes place with greater emphasis on the desmethyl component of balhimycin. Allosteric inhibitors of aspartate metabolism, such as L-lysine or L-threonine and leucine antagonists, likewise have an effect on the product spectrum.

Moreover, the product spectrum of the strain Actinomyces species Y-86,21022 can be affected by genetic measures. Mutations with mutagens of physical or chemical type known per se in combination with suitable selection methods, for example antimetabolite resistance, lead to mutants which produce the desired secondary components in greatly increased amounts or exclusively.

The separation of the glycopeptides mentioned is preferably carried out by means of cation exchangers in buffer systems having a high content of organic solvents. Suitable solvents are, for example, water-miscible organic solvents such as lower alcohols, acetone, acetonitrile, glycol, dioxane, dimethyl sulfoxide, formamide and the like, but also aqueous urea solutions. Preferred solvents are methanol, ethanol, isopropanol and acetone. Particularly suitable solvent contents are 5–95% of organic solvents in the aqueous buffer solutions, particularly preferred contents are between 25 and 85%. Since the separation effect somewhat improves with increasing solvents content, the separation is expediently carried out in practice with a content of organic solvent of not below 35%.

Another possibility for separation on a scale which can be carried out industrially consists in using "reverse phases" and improving the sharpness of separation by suitable measures. Such measures are the use of additives such as salts, for example phosphate buffer and others or of chaotropic substances such as urea, $KClO_4$ or other agents such as complexing agents and ion-pairing agents, inter alia, in the eluents.

An alternative step for the isolation of the compounds according to the invention is crystallization. In this case, the tendency of the compounds according to the invention to crystallize in the vicinity of the iso-electric points, and their dependence on solvent admixtures in the mother liquor and on the type of counter ions is utilized. For example, compounds according to the invention in aqueous solution can be brought to crystallization by addition of water-soluble organic solvents such as, for example, ethanol or isopropanol.

Alternatively, the compounds present in aqueous acidic solution are brought to crystallization by increasing the pH, for example by means of addition of $NH_3$. The crystalline compounds obtained, such as, for example, ureidobalhimycin, which crystallizes in the non-centrosymmetrical space group P1 with 2 molecules in the elemental cell and the cell constants a=17.909 Å, b=18.466 Å, c=18.873 Å, α=96.65, β=114.15, γ=114.78°, also belong to the present invention.

Another process for the preparation of desmethylleucyl-balhimycin consists in carrying out an Edman degradation with balhimycin or with desmethylbalhimycin (cf. "Practical Protein Chemistry, A Handbook" A. Darbre, page 345 ff., John Wiley & Sons, 1987).

An additional process for the preparation of desglucobalhimycin comprises carrying out a hydrolytic cleavage with balhimycin. A particularly preferred hydrolysis agent is 4N or more highly concentrated trifluoroacetic acid, in particular even at slightly elevated temperature.

An additional process for the preparation of desmethyldesglucobalhimycin comprises carrying out a hydrolytic cleavage with desmethylbalhimycin. A particularly preferred hydrolysis agent is 4N or more highly concentrated trifluoroacetic acid, in particular at room temperature or slightly elevated temperature.

An additional process for the preparation of ureidobalhimycin comprises reacting balhimycin with isocyanates such as, for example, potassium isocyanate or with urea. This reaction can be carried out, for example, in aqueous solution within a wide pH range, preferably in the range between pH 4 and 8.

The novel compounds according to the invention are closely related to the glycopeptide antibiotic balhimycin and are structurally derived from this. They can be characterized in detail as follows:

a) Desmethylbalhimycin is formed by the strain Y-86, 21022 (DSM 5908) and has the following properties:

Empirical formula: $C_{65}H_{71}Cl_2N_9O_{24}$ determined by FAB mass spectrometry: M+H$^+$=1432.4 for the isotope: $^{12}C_{65}{}^{1}H_{71}{}^{35}Cl_2{}^{14}N_9{}^{16}O_{24}$;

Chemical molecular weight: 1433.25 Da

Amino acid analysis (after hydrolysis in 5M hydrochloric acid at 100° C., 20 hours): Aspartic acid, leucine, besides other unusual ninhydrin-positive substances UV maxima: 281 nm (log E 3.8)

Desmethylbalhimycin thus differs from balhimycin in that it contains leucine instead of N-methylleucine.

b) Desmethylleucylbalhimycin is produced by means of the strain Y-86,21022 (DSM 5908) and has the following properties:

Empirical formula: $C_{59}H_{60}Cl_2N_8O_{23}$ determined by FAB mass spectrometry: M+H$^+$=1319.3 for the isotope: $^{12}C_{59}{}^{1}H_{60}{}^{35}Cl_2{}^{14}N_8{}^{16}O_{24}$;

Chemical molecular weight: 1320.08 Da

Amino acid analysis (after hydrolysis in 5M hydrochloric acid at 100° C., 20 hours): Aspartic acid, in addition to unusual ninhydrin-positive substances. Absent: leucine and N-methylleucine UV maxima: 281 nm (log E 3.8)

Desmethylleucylbalhimycin differs from balhimycin by N-methylleucine being absent.

c) Desglucobalhimycin is formed by the Actinomycetes strain Y-86.21022 (DSM 5908), and has the following properties:

Empirical formula: $C_{60}H_{63}Cl_2N_9O_{19}$ determined by FAB mass spectrometry: M+H$^+$=1284.4 for the isotope: $^{12}C_{60}{}^{1}H_{63}{}^{35}Cl_2{}^{14}N_8{}^{16}O_{19}$;

Chemical molecular weight: 1285.12 Da

Amino acid analysis (after hydrolysis in 5M hydrochloric acid at 100° C., 20 hours): Aspartic acid, N-methylleucine in addition to unusual ninhydrin-positive substances. UV maxima: 279 nm (log ε 3.8)

Desglucobalhimycin differs from balhimycin by the absence of a glucose residue.

d) Ureidobalhimycin is formed from the Actinomycetes strain Y-86,21022 (DSM 5908) and has the following properties:

Empirical formula: $C_{67}H_{74}Cl_2N_{10}O_{25}$ determined by FAB mass spectrometry: M+H$^+$=1489.4 for the isotope: $^{12}C_{67}{}^{1}H_{74}{}^{35}Cl_2{}^{14}N_{10}{}^{16}O_{25}$;

Chemical molecular weight: 1490.29 Da UV maxima 280 nm (log ε:3.8)

Ureidobalhimycin is the cyclic ureide of the antibiotic balhimycin on carbon atoms 3 and 4 of dehydrovancosamine.

e) Methylbalhimycin is formed from Actinomyces strain Y-86,21022 (DSM 5908) and has the following properties:

Empirical formula: $C_{67}H_{75}Cl_2N_9O_{24}$ determined by FAB mass spectrometry: M+H$^+$=1460.45 for the isotope: $^{12}C_{67}{}^{1}H_{75}{}^{35}Cl_2{}^{14}N_9{}^{16}O_{24}$;

f) Balhimycin R is formed from Actinomyces strain Y-86,21022 (DSM 5908) and has the following properties:

Empirical formula: $C_{72}H_{83}Cl_2N_9O_{28}$ determined by FAB mass spectrometry: M+H$^+$=1592.48 for the isotope: $^{12}C_{72}{}^{1}H_{83}{}^{35}Cl_2{}^{14}N_9{}^{16}O_{24}$;

Chemical molecular weight: 1593.41 Da. UV maxima 280 nm (log ε=3.8)

Balhimycin R differs from balhimycin by an additional rhamnosyl radical.

g) Desmethyl-desglucobalhimycin is formed from Actinomyces strain Y-86, 21022 (DSM 5908) and has the following properties:

Empirical formula: $C_{59}H_{61}Cl_2N_9O_{19}$, determined by FAB mass spectrometry: M+H$^+$=1270.35 for the isotope: $^{12}C_{59}{}^{1}H_{61}{}^{35}Cl_2{}^{14}N_9{}^{16}O_{19}$;

Chemical molecular weight: 1271.09 UV maxima 280 nm (log ε=3.8).

h) Balhimycin V is formed from the Actinomyces strain Y-86, 21022 (DSM 5908) and has the following properties:

Empirical formula: $C_{73}H_{84}Cl_2N_{10}O_{26}$ determined by FAB mass spectrometry: M+H$^+$=1587.50 for the isotope: $^{12}C_{73}{}^{1}H_{84}{}^{35}Cl_2N_{10}O_{26}$;

Chemical molecular weight: 1588.44 Da. UV maxima 280 nm (log ε=3.8).

Balhimycin V differs from balhimycin by an additional 4-dehydrovancosaminyl radical.

The compounds according to the invention are colorless substances soluble in water or in aqueous solutions, which are comparatively surprisingly stable in the form of a solid or in solution.

The following Table 1 shows some biological data:

Minimum bacteriostatic inhibitory concentrations in micrograms per milliliter determined by means of the Agar dilution method:

TABLE 1

| | | Desmethyl-balhimycin | Desmethyl-leucyl-balhimycin | Desgluco-balhimycin |
|---|---|---|---|---|
| Staph. aureus | SG 511 | 0.1 | 3 | 0.2 |
| Staph. aureus | 285 | 0.1 | 6 | 0.2 |
| Staph. aureus | 503 | 0.05 | 6 | 0.1 |
| Strept. pyogenes | 308 A | 0.05 | 12.5 | 0.1 |
| Strept. pyogenes | 77 A | 0.05 | 3 | 0.1 |
| Strept. faecium | D | 0.2 | 6 | 0.2 |
| Escherichia coli | DC 2 | 10 | >100 | >100 |
| Bact. fragilis | 312 | 100 | 50 | 25 |
| Bact. fragilis | 960 | 25 | 50 | 25 |
| Bact. fragilis | 1313 | 50 | 100 | 25 |
| Bact. vulgatus | 1446 | 50 | 100 | >100 |
| Peptostrept. anaerob. | 932 | 25 | 50 | 0.4 |
| Propioni acnes | 6916 | 0.8 | 6 | 0.2 |
| Propioni acnes | 6922 | 0.4 | 6 | 0.2 |
| Clostridium tetani ATCC 1940650 | | 50 | 50 | 0.4 |
| Clostridium perfringens | 194 | 0.2 | 6 | 0.1 |

| | | Ureido-Balhimycin | Methyl-balhimycin | Balhimycin R |
|---|---|---|---|---|
| Staph. aureus | SG 511 | 0.8 | 0.4 | 0.2 |
| Staph. aureus | 285 | 1.5 | 0.4 | 0.8 |
| Staph. aureus | 503 | 1.5 | 0.4 | 0.2 |
| Strept. pyogenes | 308 A | 0.8 | 0.4 | 0.2 |

TABLE 1-continued

| | | | | |
|---|---|---|---|---|
| Strept. pyogenes | 77 A | 0.8 | 0.4 | 0.2 |
| Strept. faecium | D | 1.5 | 0.8 | 0.4 |
| Escherichia coli | DC 2 | >100 | 25 | 50 |
| Bact. fragilis | 312 | 25 | 100 | >100 |
| Bact. fragilis | 960 | 25 | 100 | >100 |
| Bact. fragilis | 1313 | 25 | 50 | >100 |
| Bact. vulgatus | 1446 | 50 | >100 | >100 |
| Peptostrept. anaerob. | 932 | 6.2 | 0.8 | 100 |
| Propioni acnes | 6916 | 0.8 | 0.4 | 6.2 |
| Propioni acnes | 6922 | 1.5 | 0.4 | 3.1 |
| Clostridium tetani ATCC 1940650 | | 12.5 | 3.1 | 100 |
| Clostridium perfringens | 194 | 0.4 | 1.5 | — |

| | | Desmethyl-desgluco-balhimycin | Balhimycin V |
|---|---|---|---|
| Staph. aureus | SG 511 | 0.2 | 0.4 |
| Staph. aureus | 285 | 0.2 | 0.4 |
| Staph. aureus | 503 | 0.1 | 0.1 |
| Strept. pyogenes | 308 A | 0.1 | 0.05 |
| Strept. pyogenes | 77 A | 0.1 | 0.05 |
| Strept. faecium | D | 0.2 | 0.2 |
| Escherichia coli | DC 2 | >100 | >100 |
| Bact. fragilis | 312 | 50 | n.t. |
| Bact. fragilis | 960 | 25 | n.t. |
| Bact. fragilis | 1313 | 50 | n.t. |
| Bact. vulgatus | 1446 | >100 | n.t. |
| Peptostrept. anaerob. | 932 | 0.2 | n.t. |
| Propioni acnes | 6916 | 0.2 | n.t. |
| Propioni acnes | 6922 | 0.1 | n.t. |
| Clostridium tetani ATCC 19406 | | n.t. | n.t. |
| Clostridium perfringens | 194 | 0.1 | n.t. |

As can be seen from Table 1, the compounds according to the invention in particular have an outstanding action against gram-positive bacteria including the so-called methicillin-resistant Staphylococcus aureus strain (MRSA). They are therefore in particular suitable for the treatment of infectious diseases which have been caused by such microorganisms. The subject of the invention accordingly also includes pharmaceuticals containing an effective amount of a compound according to the invention and the use of the compounds for the preparation of pharmaceuticals, in particular of pharmaceuticals heaving antibiotic action; said preparation is carried out in a conventional, generally known manner.

The compounds according to the invention are furthermore also suitable for use as growth promoters in agriculture. The present invention will be illustrated in greater detail by means of the examples below and the contents of the patent claims.

EXAMPLE 1

Fermentation of the Balhimycin Components

The nutrient solution (NL 5276) is used as the main culture for the fermentation. It is composed as follows.
NL 5276: Glycerol, 99% 20 g/l of distilled water Soya peptone HySoy T 10 g/l Glucose 5 g/l $CaCO_3$ 3 g/l Yeast extract, Oxoide 3 g/l pH before sterilization 7.0 The substrates, apart from glucose, are added to 10 ml of water with stirring and made up to a volume of 18 l. The pH before sterilization is adjusted to 7.0 using dilute 20–30% strength NaOH. The amount of glucose in the mixture specified above is dissolved separately in 1 l of water and the solution is sterilized for 20 minutes at 120° C. in an autoclave and added to the sterilized mixture after cooling. Sterilization is carried out for 45 minutes at 120° C. and 1.2–1.4 bar. After cooling to operating temperature and adding the glucose solution, the fermentation volume is about 20 l with a pH of about 7.0. The C fermenter is inoculated with 500–1000 ml of preculture, which is prepared as in EP 0 468 504. Examples 2 and 3.

Fermentation conditions: Fermentation temperature 28° C. Aeration 20 l/minute=1 vvm Pressure 0.5 bar Speed 250 rpm As an antifoaming agent, if necessary, 5 ml, corresponding to 0.025% relative to the fermentation volume, of $^R$Desmophen 3600 (polyols, Bayer AG, Leverkusen) are added as a sterile water-Desmophen mixture.

The fermentation time is 96–120 hours. The pH is not corrected during the fermentation but the cultures is examined for sterility, nitrogen consumption and the formation of products by means of HPLC. It is then harvested and the cell material is removed by centrifugation.

EXAMPLE 2

Isolation of the Balhimycin Complex 10 l of filtrate from the cultures obtained as; in Example 1 are added to a previously prepared column containing 1 l of $^R$Diaion HP-20 (Mitsubishi Chem. Ind.). The loaded support is then washed with demineralized water. The balhimycin components are then eluted with a gradient containing 0–50% of isopropanol and the outflow from the column is collected in fractions. The fractions are examined for antibiotic activity and the component composition is determined by means of HPLC. First, desmethylbalhimycin-containing fractions (I), then balhimycin-richer (II) and finally desmethylleucylbalhimycin-richer fractions (III) are obtained. They are collected separately and after concentration and freeze-drying give 650 mg of I, 1.1 g of II and 380 mg of III.

EXAMPLE 3

Isolation of Desmethylbalhimycin by Ion Chromatography

A 100 ml chromatography column is packed with $^R$Fractogel EMD-$SO_3$ cation exchanger and adjusted to pH 4.8 (buffer A) with 25 mM sodium acetate buffer in 66% methanol. 650 mg of desmethylbalhimycin-containing antibiotic, obtained, for example, in accordance with Example 2 are then dissolved in approximately 100 ml of buffer A and applied to the column, and the latter is washed with 100 ml of buffer A. The antibiotic desdehydrovancosamine derivative known from the literature is found in the runnings and in the washing water.

A 0–200 mM sodium chloride gradient in buffer A, pH 5.0 is then applied. The balhimycin is eluted from the ion exchanger using 130–150 mM NaCl, and the desmethylbalhimycin using 160–175 mM NaCl solution. The corresponding fractions are each dialyzed against 1/100M acetic acid and freeze-dried. Crystallization from aqueous solution with the addition of ethanol leads to 210 mg of balhimycin acetate in 98% purity and 160 mg of desmethylbalhimycin acetate in 97% purity.

High pressure liquid chromatography (HPLC) data:

Support: ᴿLichrospher RP18, 5 μm, 250×4 mm$^2$

Elution system: 14% acetonitrile in 0.1% strength aqueous trifluoroacetic acid

Detection: UV absorption at 210 nm

Retention time: 8.3 minutes, comparison balhimycin: 10.0 minutes $[\alpha]_D^{22}$: $-77\pm2°$

EXAMPLE 4

Preparation of Pure Desmethylleucylbalhimycin 300 mg of the desmethylleucylbalhimycin-containing product III obtained as in Example 2 are additionally purified again on 100 ml of MCI gel CHP20P (Mitsubishi Chem. Ind.) in accordance with Example 2, but 10 mM $K_2HPO_4$ buffer, pH 7.6, is used as buffer A and 10 mM $K_2HPO_4$, pH 7.6 in 40% strength methanol is used as buffer B. The elution carried out in the gradient process gives fractions which are analyzed by means of HPLC. The desmethylleucylbalhimycin-containing fractions, having a purity of over 90%, are combined, concentrated in vacuo and desalted on reverse phase RP18, in a 0.05% trifluoroacetic acid/acetonitrile system. Freeze-drying of the main fractions gives 120 mg of desmethylleucylbalhimycin trifluoroacetate in 98% purity.

High pressure liquid chromatography (HPLC) data:

Support: ᴿLichrospher RP18, 5 μm, 250×4 mm$^2$

Eluent: 14% acetonitrile in 0.1% strength aqueous trifluoroacetic acid

Detection: UV absorption at 210 nm

Retention time: 16.0 minutes, comparison balhimycin: 10.0 minutes $[\alpha]_D^{22}$: $+27\pm2°$

EXAMPLE 5

Obtaining Desglucobalhimycin and Desmethyldesglucobalhimycin 300 mg of the product III obtained as in Example 2 are dissolved in water and applied to a preparative 500 ml capacity HPLC column (250-2"), which is packed with the support ᴿNucleosil 1015 C18 P (Macherey-Nagel, Düren). The latter is then eluted in the gradient process with 0-20% acetonitrile in 0.1% trifluoroacetic acid. While the antibiotics balhimycin and desmethylleucylbalhimycin are first dissolved from the support using an 8–10% solvent content, desmethyl-desglucobalhimycin and desglucobalhimycin are obtained using a 14–15% acetonitrile content. Freeze-drying of the desmethyl-desglucobalhimycin- or desglucobalhimycin-containing fractions and their rechromatography in the same system give 1.3 mg of desmethyl-desglucobalhimycin trifluoroacetate salt or 4 mg of desglucobalhimycin trifluoroacetate salt respectively.

EXAMPLE 6

Hydrolytic Degradation of Balhimycin to Desglucobalhimycin 5 g of balhimycin, obtained in accordance with the application EP 0 468 504, Example 4, are dissolved in 120 ml of 4 molar trifluoroacetic acid and allowed to react overnight at 45° C. After this period, the solvent is removed in vacuo and then by freeze-drying. The reaction mixture concentrated in this way is then dissolved in water and separated on 800 ml of MCI gel CHP20P (Mitsubishi Chem. Ind.) using the gradient system 0.1% acetic acid/0.1% acetic acid in 50% strength isopropanol. Balhimycin and desamidobalhimycin are first eluted from the column, then desglucobalhimycin and finally desamidodesglucobalhimycin. The desired fractions having a degree of purity of over 90% are collected, rechromatographed and freeze-dried. They give 1.3 g of desglucobalhimycinacetate in a purity of 98.5%.

High pressure liquid chromatography (HPLC) data

Support: ᴿLichrospher RP18, 5 μm, 250×4 mm$^2$

Eluent: 19% acetonitrile in 0.1% strength aqueous trifluoroacetic acid

Detection: UV absorption at 210 nm

Retention time: 10.0 minutes $[\alpha]_D^{22}$: $-70.5\pm2°$

EXAMPLE 7

Obtaining Ureidobalhimycin 1 g of crude balhimycin (II), obtained in accordance with Example 2, are dissolved in 25 ml of water, the pH is adjusted to 3.5 with acetic acid and the solution is applied to a previously prepared column containing 150 ml Fractogel EMD-$SO_3$ cation exchanger equilibrated at pH 3.5.

After application, the column is first washed with 200 ml of pure water, then with 200 ml of 25 mM sodium acetate buffer pH 4.0 (buffer A).

The column outflow of this buffer solution contains the ureidobalhimycin, called eluate WP. The column is then eluted by applying a 0.1M NaCl gradient in 25 mM sodium acetate, pH 4.0. Balhimycin R (eluate R) is obtained using 20–30 mM NaCl, mainly balhimycin (eluate B) using 30–70 mM NaCl and desmethyl- and methylbalhimycin (eluate M) using 80–100 mM NaCl.

For the preparation of pure ureidobalhimycin, the eluate WP is added to a nucleosil 10-$C_{18}$ AB reverse phase column (20 mm ID×250 mm length) and separated in the gradient process using the 0.1% trifluoroacetic acid/acetonitrile system-as outlined in Example 5. Freeze-drying of the ureidobalhimycin-containing fraction gives 20 mg of this antibiotic as the trifluoroacetate salt.

High pressure liquid chromatography (HPLC) data:

Support: ᴿLichrospher RP18, 5 μm, 250×4 mm$^2$

Eluent: 14% acetonitrile in 0.1% strength aqueous trifluoroacetic acid

Detection: UV absorption at 210 nm

Retention time: 13.5 min, comparison balhimycin: 10.0 min $[\alpha]_D^{24}$= $-26°$ (c=1% in water)

EXAMPLE 8

Obtaining Methylbalhimycin

The eluate M obtained as in Example 7 is purified on the 20 mm×250 mm (ID×H) ᴿNucleosil 10-$C_{18}$ AB column with the aid of the gradient system 10 mM $K_2HPO_4$, pH 7.5/45% methanol in 10 mM $K_2HPO_4$, pH 7.5.

The column outflow is controlled by the analytical HPLC system-as described below-and the methylbalhimycin-containing fractions are combined, concentrated in vacuo and desalted by adsorption on ᴿMCI gel CHP20P as in Example 6. Freeze-drying of the phosphate-free pure antibiotic solution gives 11 mg of methylbalhimycinacetate in 98% purity.

High pressure liquid chromatography (HPLC) data:

Support: ®Lichrospher RP18, 5 µm, 250×4 mm²

Eluent: 14% acetonitrile in 0.1% strength aqueous trifluoroacetic acid

Detection: UV absorption at 210 nm

Retention time: 15.8 min, in comparison to balhimycin: 10.0 min $[\alpha]_D^{24} = -59°$ (c=1% in water)

EXAMPLE 9

Hydrolytic Degradation of Desmethylbalhimycin to Desmethyl-Desglucobalhimycin 100 mg of desmethylbalhimycin, obtained according to Example 3, are dissolved in 2 ml of 90% strength trifluoroacetic acid and allowed to react at room temperature for 70 hours. The mixture is then worked up according to Example 6. 72 mg of desmethyl-desglucobalhimycin acetate are obtained in 98% purity.

High pressure liquid chromatography (HPLC) data:

Support: ®Lichrospher RP 18, 5µ, 250×4 mm²

Eluent: 19% acetonitrile in 0.1% strength aqueous trifluoroacetic acid.

Detection: UV absorption at 210 nm

Retention time: 9.1 min

EXAMPLE 10

Obtaining Balhimycin R 150 mg of the desalted and freeze-dried eluate R obtained as in Example 7 are rechromatographed on the same Fractogel column as described in Example 7. The balhimycin R now obtained in 79% purity is purified and desalted further on reverse phase ®Nucleosil 10 RP$_{18}$AB—as Example 7—in the 0.1% trifluoroacetic acid system. The freeze-dried antibiotic (52 mg) is dissolved in 3 ml of water, the pH is slowly adjusted to 6 and a further 0.6 ml of ethanol is added to the solution after crystallization commences. After crystallization is complete, the mixture is centrifuged and the crystallizate is washed with ethanol and dried in vacuo. 22 mg of balhimycin R in 99% purity result.

High pressure liquid chromatography (HPLC) data:

Support: ®Lichrospher RP18, 5 µm, 250×4 mm²

Eluent: 14% acetonitrile in 0.1% strength aqueous trifluoroacetic acid

Detection: UV absorption at 210 nm

Retention time: 7.9 min, comparison balhimycin: 10.0 min

EXAMPLE 11

Obtaining Ureidobalhimycin from Balhimycin 1500 mg of balhimycin obtained in accordance with EP 0 468 504 are dissolved in 60 ml of water, 162 mg of potassium cyanate are added, the pH is adjusted to 6 and the solution is allowed to stand for 2 hours. After this time, it is separated by preparative HPLC in the 0.1% trifluoroacetic acid system of a 500 ml capacity ®Nucleosil 1015 C18 P, 250-2" column. The ureidobalhimycin-containing fractions are collected separately from the balhimycin, freeze-dried and crystallized in water/ethanol at pH 5. Centrifugation and drying give 1.3 g of ureidobalhimycin in over 98% purity.

EXAMPLE 12

Obtaining Balhimycin V

A 100 ml chromatography column is packed with ®Fractogel EMD-SO$_3$ cation exchanger and equilibrated with 25 mM ammonium formate buffer, pH 4.2 (buffer A). 1 g of crude balhimycin (II), obtained according to Example 2, is dissolved in 100 ml of water, the solution is adjusted to pH 4 and applied to the column, and the latter is washed with 200 ml of buffer A.

A 0.5M sodium chloride gradient in buffer A, pH 4 is subsequently applied. The less basic antibiotics of the balhimycin series are eluted from the column first with a 0.34–0.36M NaCl solution of balhimycin V. The corresponding balhimycin V-containing fractions are collected and desalted as described in Example 6 on 100 ml of ®MCl gel CHP 20 P and freeze-dried. They yield 80 mg of balhimycin V acetate.

Higher pressure liquid chromatography (HPLC) data:

Support: ®Lichrospher RP, 18.5 µm, 250×4 mm²

Eluent: 14% acetonitrile in 0.1% strength aqueous trifluoroacetic acid

Detection: UV absorption at 210 nm

Retention time: 10.3 to 10.4 min, as the wider peak, comparison with balhimycin: 10 min Retention time of the reaction product of balhimycin V with potassium cyanate according to Example 10: 12.4 min Comparison with balhimycin: 10 min.

FAB mass spectrum:

Mass calculated from all molecular ions 1588 Da.

ESI mass spectrum:

Mass is calculated from all molecular ions.

MW 1588 Da (diketone form), MW 1606 Da (monohydrate),

MW 1624 Da (dihydrate)

We claim:

1. Desmethylbalhimycin, a compound of the formula I,

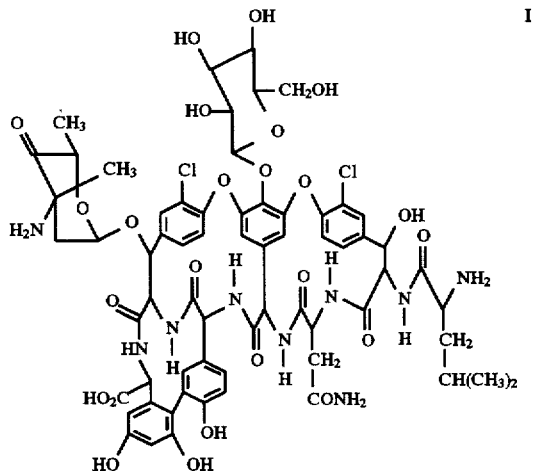

desmethylleucylbalhimycin, a compound of the formula II.

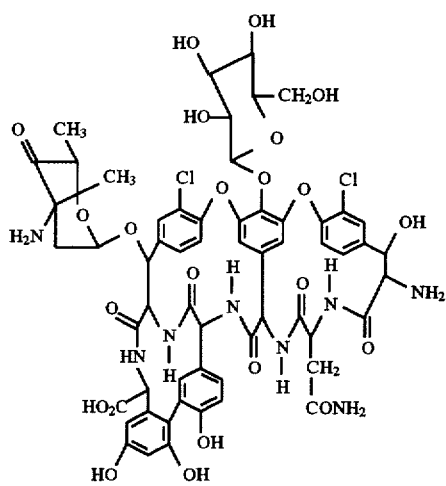

desglucobalhimycin, a compound of the formula III.

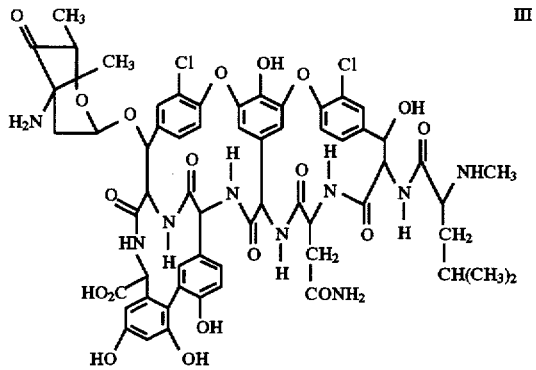

ureidobalhimycin, a compound of formula IV.

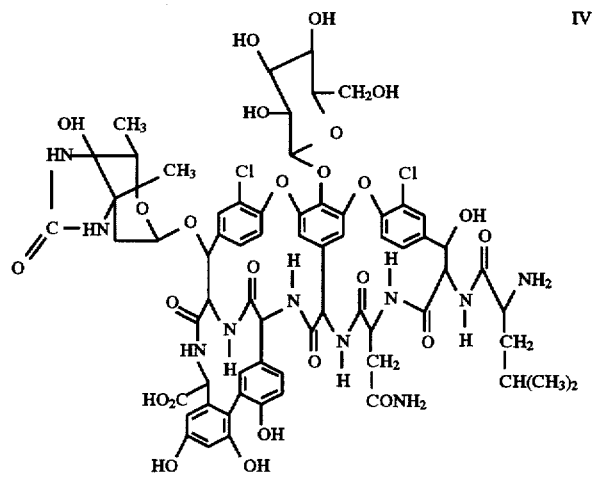

desmethyl-desglucobalhimycin, a compound of the formula

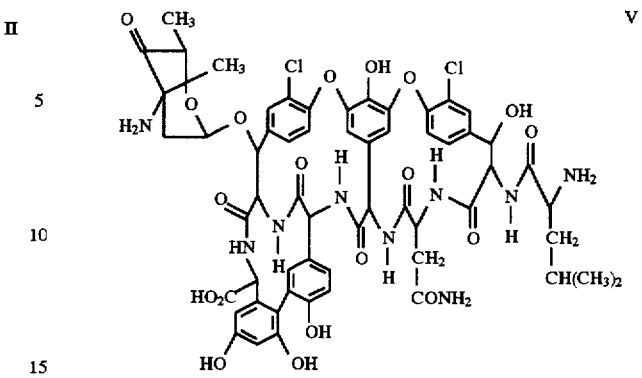

methylbalhimycin, a compound of the formula $C_{67}H_{75}Cl_2N_9O_{24}$, balhimycin R, a compound of the formula $C_{72}H_{83}Cl_2N_9O_{28}$ and balhimycin V, a compound of the formula $C_{73}H_{84}Cl_2N_{10}O_{26}$ and their hydrates and physiologically tolerable salts.

2. A compound as claimed in claim 1 in crystalline form.

3. A compound as claimed in claim 1, which can be prepared by fermentation of Actinomyces species Y-86, 21022 (DSM 5908) in an aqueous nutrient medium and subsequent isolation.

4. A process for the preparation of compounds as claimed in claim 1, which comprises culturing the microorganism Actinomyces species Y-86,21022 (DSM 5908) in an aqueous nutrient medium and then isolating and purifying the target compounds.

5. A process for the preparation of desmethylleucylbalhimycin by Edman degradation of balhimycin or of desmethylbalhimycin.

6. A process for the preparation of desglucobalhimycin by hydrolytic cleavage of balhimycin.

7. A process for the preparation of ureidobalhimycin which comprises reacting balhimycin with an isocyanate or with urea.

8. A process for the preparation of desmethyl-desglucobalhimycin by hydrolytic cleavage of desmethylbalhimycin.

9. A pharmaceutical composition containing an effective amount of at least one compound as claimed in claim 1 together with a pharmaceutically acceptable carrier.

10. A process for the preparation of pharmaceuticals which comprises bringing a compound as claimed in claim 1 into a suitable administration form, if appropriate using pharmacologically acceptable auxiliaries and/or excipients.

11. A process for the treatment of infectious diseases caused by gram-positive bacteria which comprises administering an effective amount for said treatment of a compound of the formula I, II, III, IV, or V as claimed in claim 1.

12. A process as claimed in claim 11 wherein the gram-positive bacteria is methicillin-resistant *Staphylococcus aurous* strain (MRSA).

* * * * *

UNITED STATES PATENT AND TRADEMARK OFFICE
CERTIFICATE OF CORRECTION

PATENT NO.   : 5,763,397
DATED        : June 9, 1998
INVENTOR(S)  : VERTESY et al.

It is certified that error appears in the above-identified patent and that said Letters Patent is hereby corrected as shown below:

Claim 1, column 13, lines 40-58, in the formula IV,

" 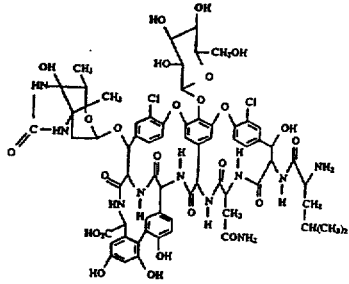 IV " should read -- 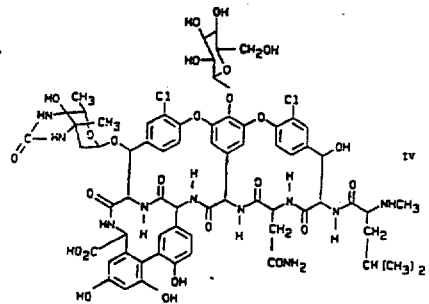 --.

Claim 1, column 13, lines 60-61, after "formula", insert --V--.

Signed and Sealed this

Fifth Day of September, 2000

Attest:

Q. TODD DICKINSON

Attesting Officer

Director of Patents and Trademarks